(12) United States Patent
Katz et al.

(10) Patent No.: US 10,321,878 B2
(45) Date of Patent: Jun. 18, 2019

(54) PULMONARY VEIN DISPLAY IN TWO DIMENSIONS

(71) Applicant: BIOSENSE WEBSTER (ISRAEL) LTD., Yokneam (IL)

(72) Inventors: Natan Sharon Katz, Atlit (IL); Lior Zar, Poria Illit (IL); Benjamin Cohen, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 15/388,029

(22) Filed: Dec. 22, 2016

(65) Prior Publication Data
US 2018/0177467 A1   Jun. 28, 2018

(51) Int. Cl.
| | |
|---|---|
| *A61B 5/00* | (2006.01) |
| *G06T 11/00* | (2006.01) |
| *A61B 90/00* | (2016.01) |
| *G06T 7/73* | (2017.01) |
| *A61B 5/02* | (2006.01) |
| *A61B 18/14* | (2006.01) |
| *G06T 7/00* | (2017.01) |

(Continued)

(52) U.S. Cl.
CPC .......... *A61B 5/7425* (2013.01); *A61B 5/0084* (2013.01); *A61B 5/02007* (2013.01); *A61B 5/4836* (2013.01); *A61B 18/14* (2013.01); *A61B 18/1492* (2013.01); *A61B 90/37* (2016.02); *G06T 7/0014* (2013.01); *G06T 7/74* (2017.01); *G06T 11/00* (2013.01); *G06T 11/60* (2013.01); *G06T 15/08* (2013.01); *A61B 2018/00345* (2013.01); *A61B 2018/00375* (2013.01); *A61B 2018/00577* (2013.01); *A61B 2018/00779* (2013.01); *A61B 2018/00886* (2013.01); *A61B 2090/065* (2016.02); *A61B 2090/364* (2016.02); *A61B 2090/373* (2016.02); *G06T 11/008* (2013.01); *G06T 2207/30101* (2013.01); *G06T 2210/41* (2013.01); *G06T 2219/021* (2013.01)

(58) Field of Classification Search
CPC ..... A61B 5/7425; A61B 18/14; A61B 5/4836; A61B 5/02007; A61B 2018/00345; A61B 2018/00577; G06T 7/74; G06T 7/0014; G06T 15/08; G06T 11/60; G06T 2207/30101; G06T 2210/41
See application file for complete search history.

(56) References Cited

U.S. PATENT DOCUMENTS

| | | | |
|---|---|---|---|
| 7,961,924 B2 | 6/2011 | Viswanathan | |
| 8,135,185 B2 | 3/2012 | Blume | |

(Continued)

FOREIGN PATENT DOCUMENTS

EP     2 800 063 A2    11/2014

OTHER PUBLICATIONS

Synapse 3D ("Synapse 3D Feature Overview—from Fujifilm Medical Systems", Fujifilm Medical Systems USA, published on YouTube on Sep. 28, 2012 at https://www.youtube.com/watch?v=zqW4Qr6Z6yw, video length: 4:50) (Year: 2012).*

*Primary Examiner* — William A Beutel
(74) *Attorney, Agent, or Firm* — Volpe and Koenig, P.C.

(57) ABSTRACT

A method for data display includes acquiring a three-dimensional (3D) map of a lumen inside a body of a subject, transforming the 3D map of the lumen into a two-dimensional (2D) image by projecting the 3D map onto an annulus, and presenting the 2D image on a display screen.

15 Claims, 5 Drawing Sheets

(51) Int. Cl.
*G06T 11/60* (2006.01)
*G06T 15/08* (2011.01)
*A61B 18/00* (2006.01)

(56) References Cited

U.S. PATENT DOCUMENTS

| | | | |
|---|---|---|---|
| 2005/0283075 A1* | 12/2005 | Ma | G01S 15/8979 600/441 |
| 2006/0025679 A1 | 2/2006 | Viswanathan et al. | |
| 2006/0036163 A1 | 2/2006 | Viswanathan | |
| 2006/0058647 A1* | 3/2006 | Strommer | A61B 5/06 600/434 |
| 2009/0016483 A1* | 1/2009 | Kawasaki | A61B 5/02007 378/4 |
| 2012/0189178 A1* | 7/2012 | Seong | G06T 11/008 382/128 |
| 2013/0123598 A1* | 5/2013 | Jenkins | A61B 5/055 600/374 |
| 2014/0058387 A1 | 2/2014 | Kruecker et al. | |
| 2016/0155232 A1* | 6/2016 | Sela | G06T 7/0012 382/103 |
| 2016/0331262 A1* | 11/2016 | Kuck | A61B 5/04085 |
| 2017/0014202 A1* | 1/2017 | Ransbury | A61B 90/30 |

* cited by examiner

PULMONARY VEIN DISPLAY IN TWO DIMENSIONS

FIELD OF THE INVENTION

The present invention relates generally to medical ablation procedures, and particularly to the display of a medical ablation procedure.

BACKGROUND

Catheter ablation is a minimally invasive procedure used to remove or terminate a faulty electrical pathway from sections of the heart of a patient who is prone to developing cardiac arrhythmias.

U.S. Patent Application 2013/0123598 describes an MRI-compatible catheter, which includes an elongated flexible shaft having opposite distal and proximal end portions. A handle is attached to the proximal end portion and includes an actuator in communication with the shaft distal end portion that is configured to articulate the shaft distal end portion. The distal end portion of the shaft may include an ablation tip and includes at least one RF tracking coil positioned adjacent the ablation tip that is electrically connected to an MRI scanner. The at least one RF tracking coil is electrically connected to a circuit that reduces coupling when the at least one RF tracking coil is exposed to an MRI environment. Each RF tracking coil is a 1-10 turn solenoid coil, and has a length along the longitudinal direction of the catheter of between about 0.25 mm and about 4 mm.

U.S. Patent Application 2012/0189178 describes a method and an apparatus for automatically generating an optimal 2-dimensional (2D) medical image from a 3D medical image, at least one virtual plane crossing a 3D volume is generated from 3D volume image data for showing part of a patient's body in a 3D manner, at least one 2D image representing a cross section of the part of the patient's body is generated by applying the 3D volume image data to the virtual plane, and a 2D image suitable for diagnosis of the patient having a feature most similar to a target feature from among the at least one 2D image is output.

U.S. Pat. No. 8,135,185 describes a method of finding the location of an occluded portion of a blood vessel relative to a three-dimensional angiographic image of a subject's vasculature includes identifying the location of the occluded portion of the blood vessel on each of a series of displayed two dimensional images derived from the three dimensional image data in planes substantially transverse to direction of the occluded portion of the vessel. The identified locations in the occluded portion of the vessel can then be used to determine the path of the occluded portion of the vessel.

U.S. Pat. No. 7,961,924 describes a method and system for determining the three-dimensional location and orientation of a medical device distal end using a single-plane imaging system, using a computational model of the medical device and a transfer function for the medical device describing local device shape and orientation in response to user or computer determined inputs. The method allows guidance of an interventional medical system to a set of target points within the patient using a single-projection imaging system.

SUMMARY

Embodiments of the present invention that are described hereinbelow provide a method for viewing a lumen of a patient.

There is therefore provided, in accordance with an embodiment of the present invention, a method for data display, including acquiring a three-dimensional (3D) map of a lumen inside a body of a subject, transforming the 3D map of the lumen into a two-dimensional (2D) image by projecting the 3D map onto an annulus, and presenting the 2D image on a display screen.

In a disclosed embodiment, presenting the 2D image includes presenting a stationary 2D image.

In some embodiments a 3D image of the 3D map and the stationary 2D image are simultaneously presented on adjacent parts of the display screen. Additionally or alternatively, the 2D image may be kept stationary while manipulating the 3D image.

In a disclosed embodiment acquiring the 3D map includes acquiring a 3D map of a lumen undergoing an ablation procedure, wherein the ablation procedure may include ablating a pulmonary vein of a heart. Additionally or alternatively, the method includes calculating a path for the ablation procedure for a given starting point on the pulmonary vein, and displaying an image of the path on a 3D image of the 3D map and on the 2D image.

In some embodiments a calculated location and an extent of an ablation lesion are displayed on a 3D image of the 3D map and on the 2D image. Additionally or alternatively, a recommended starting point for a further ablation is calculated based on at least one of the calculated location and the extent of the ablation lesion, and the method includes displaying the recommended starting point as a mark on the 3D image and on the 2D image.

In a further embodiment a completion of the ablation procedure is determined in response to presenting an image of a contiguous closed lesion on the 2D image.

There is also provided, in accordance with an embodiment of the present invention, an apparatus for displaying data, including a display screen and a processor which is configured to acquire a 3D map of a lumen inside a body of a subject, transform the 3D map of the lumen into a 2D image by projecting the 3D map onto an annulus and present the 2D image on the display screen.

In another embodiment the 2D image is stationary.

In yet another embodiment the processor is configured to present a 3D image of the 3D map and the 2D image simultaneously on adjacent parts of the display screen. Additionally or alternatively, the processor is configured to keep the 2D image stationary while manipulating the 3D image.

In still other embodiments the 3D map includes a 3D map of a lumen undergoing an ablation procedure, and the ablation procedure may include ablating a pulmonary vein of a heart. Additionally or alternatively, the processor is configured to calculate a path for the ablation procedure for a given starting point on the pulmonary vein, and to display an image of the path on a 3D image of the 3D map and on the 2D image.

In another embodiment the processor is configured to display a calculated location and an extent of an ablation lesion on a 3D image of the 3D map and on the 2D image. Additionally or alternatively, the processor is configured to calculate a recommended starting point for a further ablation based on at least one of the calculated location and the extent of the ablation lesion, and to display the recommended starting point as a mark on the 3D image and on the 2D image.

In an embodiment the processor is configured to determine a completion of the ablation procedure in response to presenting an image of a continuous closed lesion on the 2D image.

The present invention will be more fully understood from the following detailed description of the embodiments thereof, taken together with the drawings in which:

OVERVIEW

Figure 1:
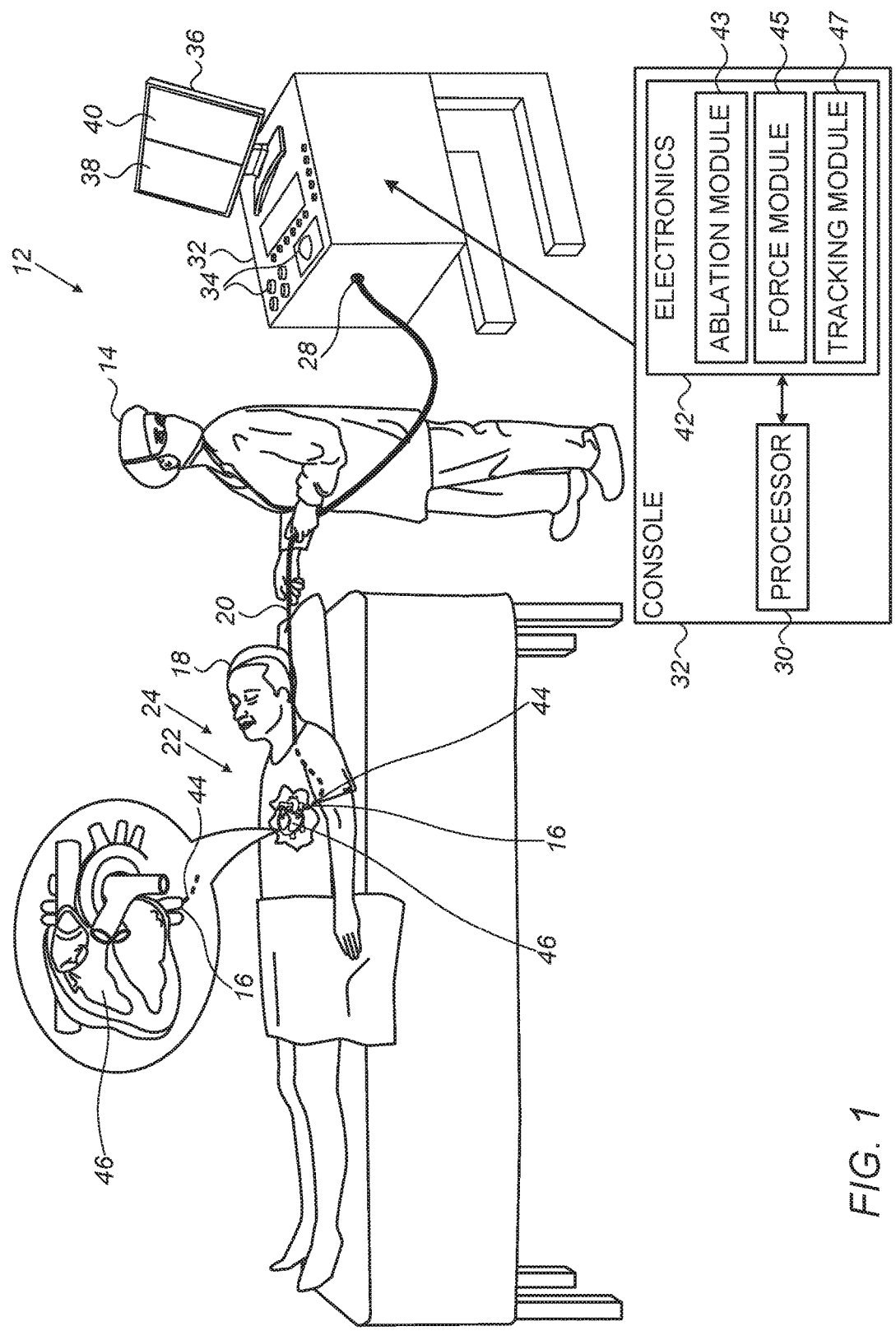
FIG. 1 is a schematic illustration of an ablation procedure of a pulmonary vein, according to an embodiment of the present invention.

One of the problems during a catheter ablation procedure, such as ablation of the pulmonary vein, is visualization of the procedure. Typically, the pulmonary vein is presented as a three-dimensional (3D) image, and as a surgeon performs the ablation he/she re-positions and/or rotates and/or changes the magnification of the image to observe the progress of the procedure. Surgeons using this method for tracking the procedure have found the use and manipulation of a 3D image, typically while ablating, both complicated and difficult to execute efficiently.

An embodiment of the present invention solves this problem by acquiring a 3D map of a lumen, such as the pulmonary vein, that is inside a body of a subject. The 3D map is transformed into a two-dimensional (2D) image by projecting the 3D map onto an annulus, and the 2D image is presented to the surgeon on a display screen.

Using this method, the surgeon is able to view and manipulate a 3D image of a region of an ablation, as described above, while being simultaneously presented with a stationary two-dimensional (2D) image of the region.

In one embodiment, in the ablation of a pulmonary vein, the region of ablation comprises a cylindrical structure. A processor acquiring the 3D image transforms this cylindrical structure into a 2D annulus, with the two edges of the cylindrical structure transformed into the inner and outer circumferences of the annulus, and the area of the cylindrical structure transformed into the area of the annulus. The display screen that the surgeon observes during the ablation procedure, is divided into two areas: The manipulable 3D image of the region of ablation, together with other parts of the heart, is displayed in one area of the display screen, whereas the stationary 2D annulus is displayed in the other area.

In another embodiment, once the surgeon has determined the starting point of the ablation, the processor calculates, based on this starting point and on the known geometry of the pulmonary vein, a recommended path for the ablation procedure. This path is marked both in the 3D image and in the 2D annulus in order to guide the surgeon. The recommended path is a path around the pulmonary vein, such that, when the ablation procedure has been completed, a heartbeat activation wave will be blocked.

In yet another embodiment, while an ablation lesion is growing during the procedure, the processor calculates the locations where the surgeon should start the next ablation lesion in order to ensure the elimination of any gaps between the ablation lesions. There will usually be two such locations, one on either side of the existing ablation lesions. These locations are marked on both the 3D image and the 2D annulus, and they are re-calculated and moved as the ablation lesions grow.

In a disclosed embodiment, the dimensions of any given ablation lesion is calculated by the processor, using measurements of force exerted by the tip of the catheter, the radio-frequency power emitted from the tip of the catheter, and the elapsed time for the lesion. In a successful ablation procedure, the surgeon sees a contiguous chain of calculated images of ablation lesions growing around the pulmonary vein, until a complete ring of ablation lesions has been formed. The visualization of both the progress and the completeness of the ring of calculated images of ablation lesions is greatly facilitated by the display of the 2D annulus, as the entire ablated region can be seen at once.

SYSTEM DESCRIPTION

FIG. 1 is a schematic illustration of an invasive medical procedure using apparatus 12, according to an embodiment of the present invention. The procedure is performed by a surgeon 14, and, by way of example, the procedure in the description hereinbelow is assumed to comprise ablation of a portion of a pulmonary vein 16 of a heart 46 of a human patient 18. However, it will be understood that embodiments of the present invention are not just applicable to this specific procedure, and may include substantially any procedure on biological tissue.

In order to perform the ablation, surgeon 14 inserts a probe 20, typically a catheter, into a lumen of the patient, so that a distal end 22 of the probe enters pulmonary vein 16 of the patient. Distal end 22 comprises electrodes 24 mounted on the outside of the distal end, the electrodes contacting respective locations of pulmonary vein 16. A proximal end 28 of probe 20 is coupled to a console 32 of apparatus 12.

Apparatus 12 is controlled by a processor 30, which is located in console 32. Console 32 comprises controls 34 which are used by surgeon 14 to communicate with processor 30. During the procedure, processor 30 typically tracks a location and an orientation of distal end 22 of the probe, using any method known in the art. For example, processor 30 may use a magnetic tracking method, wherein magnetic transmitters external to patient 18 generate signals in coils positioned in distal end 22. The Carto® system produced by Biosense Webster, of Diamond Bar, Calif., uses such a tracking method.

The software for processor 30 may be downloaded to the processor in electronic form, over a network, for example. Alternatively or additionally, the software may be provided on non-transitory tangible media, such as optical, magnetic, or electronic storage media. Processor 30 is coupled to a display screen 36, which is divided into a left display 38 and a right display 40, as is detailed below. While for simplicity the description herein assumes that the screen is divided into a left and a right display, it will be understood that the scope of the present invention includes any other convenient method for screen division and image display, such as an upper and lower display, or a first screen and a separate second screen.

In order to operate apparatus 12, processor 30 communicates with electronics 42, which has a number of modules used by the processor to operate the apparatus. Thus, electronics 42 comprises modules such as an ablation module 43, a force module 45 for measuring the force on distal end 22, and a tracking module 47 for operating the tracking method used by processor 30. The modules may comprise hardware as well as software elements. Proximal end 28 of probe 20, coupled to console 32, is further coupled to the modules of electronics 42.

Processor 30 uses results of measurements from the modules, such as a force exerted by tip 44 of distal end 22, a radio-frequency power emitted from the tip, an elapsed time of the ablation, and a location of the tip, to calculate and to display graphically the progress of the ablation procedure on display screen 36, as is detailed below.

FIGS. 2-8 show, with reference to FIG. 1, display screen 36 as seen by surgeon 14 during an ablation procedure of pulmonary vein 16 of patient 18, in accordance with embodiments of the invention. Left display 38 shows 3D images of pulmonary vein 16 and heart 46 of patient 18, and right display 40 shows a 2D image of a selected portion of pulmonary vein 16. As is described below, the 3D image in left display 38 is typically manipulable, while the 2D image in right display 40 is typically stationary. Corresponding items in left display 38 and right display 40 are labelled with the same number, with letter "L" and "R" indicating left and right display, respectively. Display screen 36 may display additional information relating to the ablation procedure, for example, an elapsed time, and a power dissipated by electrodes performing the ablation. For simplicity, such additional information is not presented in the figures.

Figure 2:
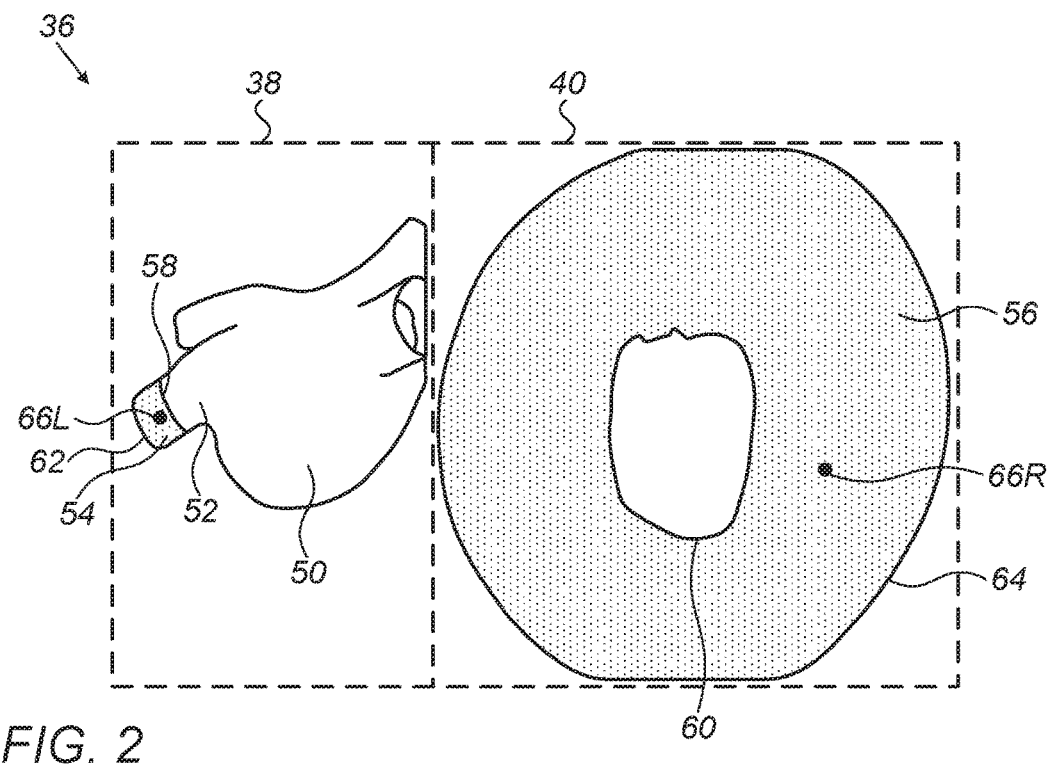
FIGS. 2-8 show a display screen as seen by a surgeon during an ablation procedure of a pulmonary vein of a subject, in accordance with an embodiment of the invention.

FIG. 2 illustrates in left display 38 a 3D image 50 of heart 46 and a 3D image 52 of pulmonary vein 16 of heart 46. A cylindrical region 54 of image 52 corresponds to the region of pulmonary vein 16 where surgeon 14 implements the ablation procedure. During the procedure, processor 30 projects cylindrical region 54 to a 2D annulus 56 in right display 40, with an edge 58, proximal to image 50, of cylindrical region 54, projected to an inner circumference 60 of annulus 56, and an edge 62, distal to image 50, projected to an outer circumference 64 of annulus 56. Surgeon 14 has positioned tip 44 of probe 20 to touch pulmonary vein 16, with the position indicated in left display 38 by a fiducial 66L, and in right display 40 by a fiducial 66R. Fiducials 66L and 66R, and the other fiducials referred to hereinbelow, are typically presented on screen 36 as icons corresponding to tip 44.

Figure 3:
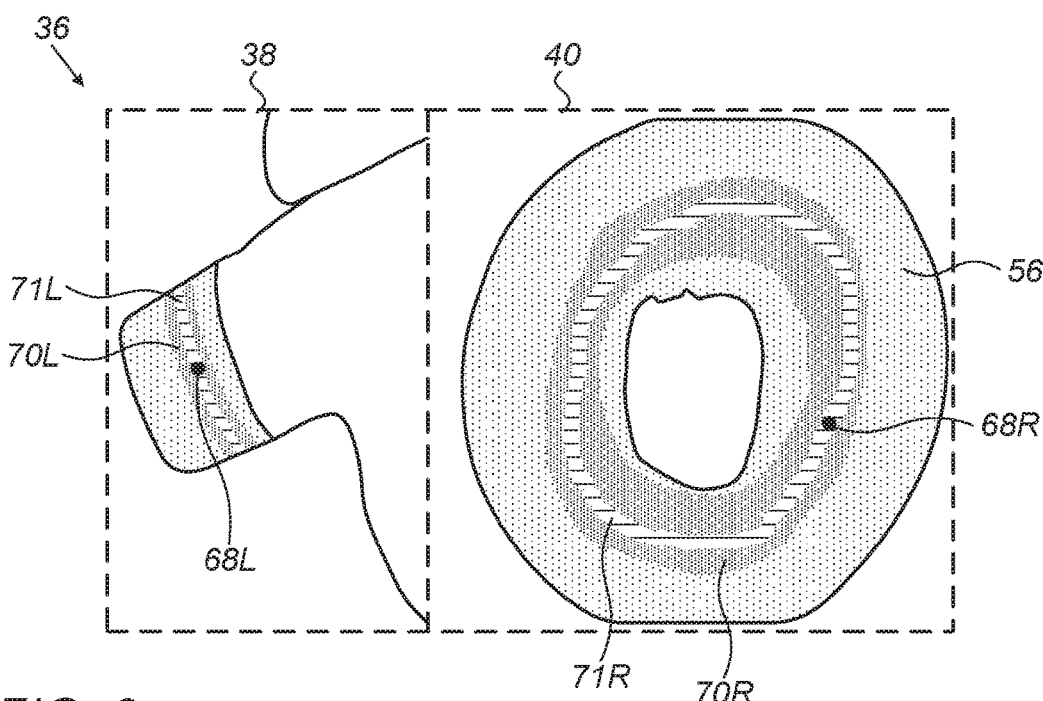

FIG. 3 illustrates display screen 36 after surgeon 14 has selected a starting point for tip 44 to begin ablation, but before initiating the ablation. Fiducials 68L and 68R indicate the selected starting point of the ablation in left display 38 and right display 40, respectively. Once the starting point is selected, processor 30 calculates a recommended closed ablation path based on the starting point and the known 3D dimensions of pulmonary vein 16. The recommended closed path is calculated based on criteria chosen by surgeon 14, with the criteria being, for example, that the closed path is a shortest path around the pulmonary vein, or that the closed path is a fixed distance from the base of the pulmonary vein. The recommended closed path is displayed as regions 70L and 70R in left display 38 and right display 40, respectively. Region 70L is a band within image 54, corresponding to a recommended path around pulmonary vein 16, and region 70R is a ring within annulus 56. Within each of regions 70L and 70R there is marked a narrower ring 71L and 71R further assisting surgeon 14 in directing the ablation procedure. Ring 71L and 71R are optimal paths for the ablation, and the width of regions 70L and 70R are typically set by surgeon 14 based on the maximum distance he/she is willing to deviate from rings 71L and 71R. The recommended ablation path is a closed path around pulmonary vein 16, such that, when the ablation procedure has been completed, a heartbeat activation wave is blocked.

Figure 4:
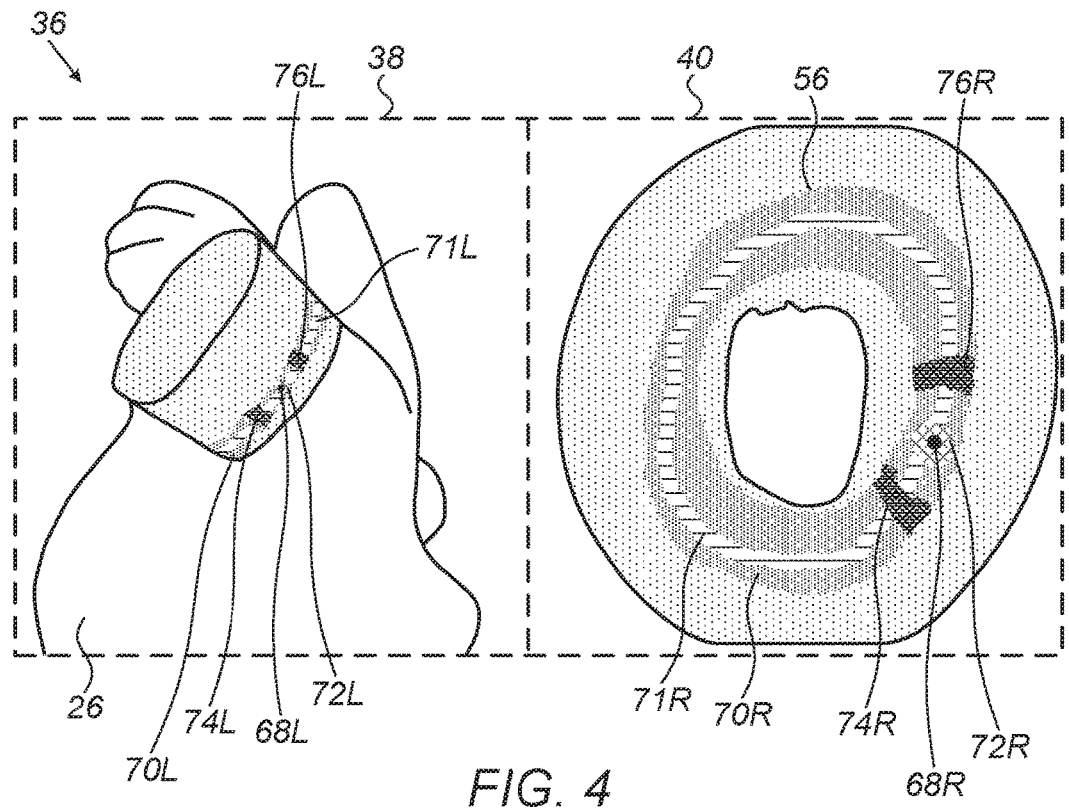

FIG. 4 illustrates display screen 36 at the start of the ablation. Left display 38 and right display 40 show calculated ablation lesion images 72L and 72R for the first ablation growing, with reference to FIG. 3, from starting point fiducials 68L and 68R, respectively. On screen 36 images of different elements are typically differentiated by different colors. In the figures of the present application, images of different elements are differentiated by different types of shading. Thus, completed ablation lesion regions may be imaged as red on screen 36, and are shown has cross-hatched in the figures.

The dimensions of lesion images 72L and 72R are calculated by processor 30, using measurements of force exerted by tip 44, radio-frequency power emitted from the tip, and elapsed ablation time. In addition, processor 30 calculates two next recommended ablation positions in regions 70L and 70R and shows them as marks 74L and 76L on left display 38 and as marks 74R and 76R on right display 40. The next recommended ablation positions provide the surgeon with two optional starting positions for a subsequent ablation. In a disclosed embodiment these positions are calculated to be a fixed distance from the edge of outermost ablations. The fixed distance may be chosen by surgeon 14. In one embodiment the fixed distance has a default value of 3 mm, but the distance may be smaller or larger than this value.

The next recommended positions depend on the location and size of the ablation lesion. Surgeon 14 may slide tip 44 along the pulmonary vein, and simultaneously ablate using the tip. Alternatively or additionally, the surgeon may keep the tip stationary while ablating. In either case, as the ablation lesion grows, the next recommended positions are re-calculated and "pushed out." The images presented on screen 36 are generated in real-time, and surgeon 14 is aided by the real-time presentation of the lesion images 72L and 72R on the two displays. Surgeon 14 terminates the ablation based on his/her judgment and the images on screen 36, but no later than when the ablation lesion images on screen 36 reach the edge of regions 70L and 70R. Both the real-time visualization of the ablation lesions and the indication of next ablation positions are applied continuously in the ablation procedure.

Referring back to FIGS. 2 and 3, it is apparent in left display 38 that surgeon 14 has rotated, using controls 34, the 3D image as the ablation procedure progresses. However, during this rotation, processor 30 ensures that annulus 56 in right display 40 remains stationary, thus aiding surgeon 14 in an easy and fast observation of the progress of the ablation procedure. It is of great help for surgeon 14 to be able to rotate or otherwise manipulate the 3D image at will in left display 38, while at the same time observing a fully stationary 2D image in right display 40.

Figure 5:
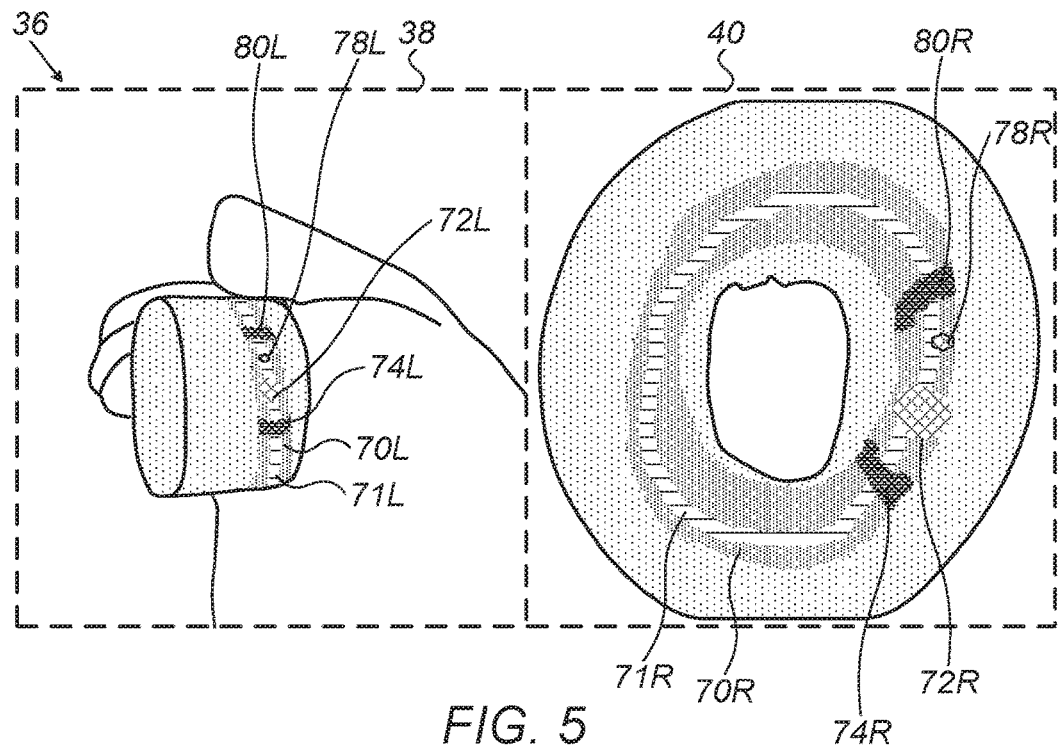

FIG. 5 illustrates display screen 36 at the completion of the first ablation lesion, displayed as lesion images 72L and 72R, and the start of a second ablation lesion, shown as lesion images 78L and 78R. The second ablation is implemented at the "upper" recommended next position, shown as marks 76L and 76R, respectively, in FIG. 4. Since the ablation procedure is continuing, processor 30 calculates new recommended next positions. Thus, processor 30 calculates a new, shifted upper recommended next position to reflect the presence of a second ablation lesion, and displays it as marks 80L and 80R. The "lower" recommended next position 74L, 74R is not changed.

Figure 6:
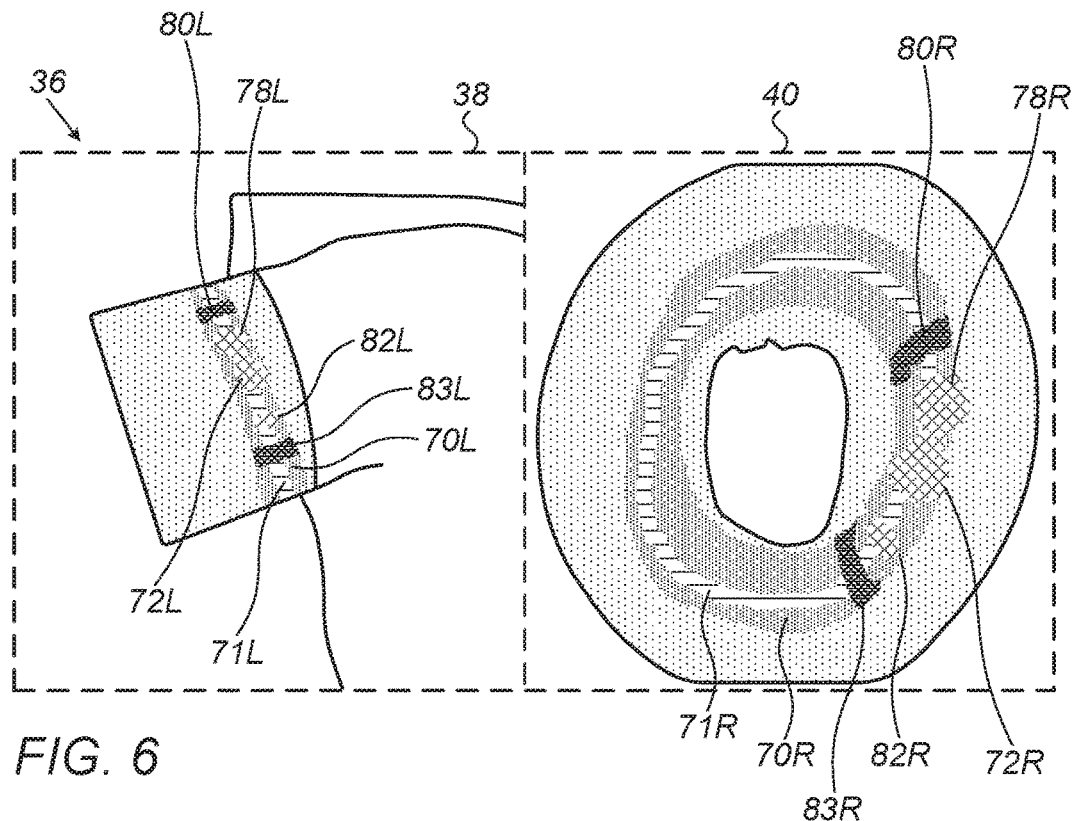

FIG. 6 illustrates display screen 36 after the first ablation lesion, shown as lesion images 72L and 72R, and the second ablation lesion, shown as lesion images 78L and 78R, have reached their final sizes, melding into each other, and a third ablation lesion, shown as lesion images 82L and 82R, has started forming. In this case processor 30 changes the position of the lower recommended position to a new position 83L, 83R, while leaving the position of the upper recommended position 80L, 80R unchanged.

Figure 7:
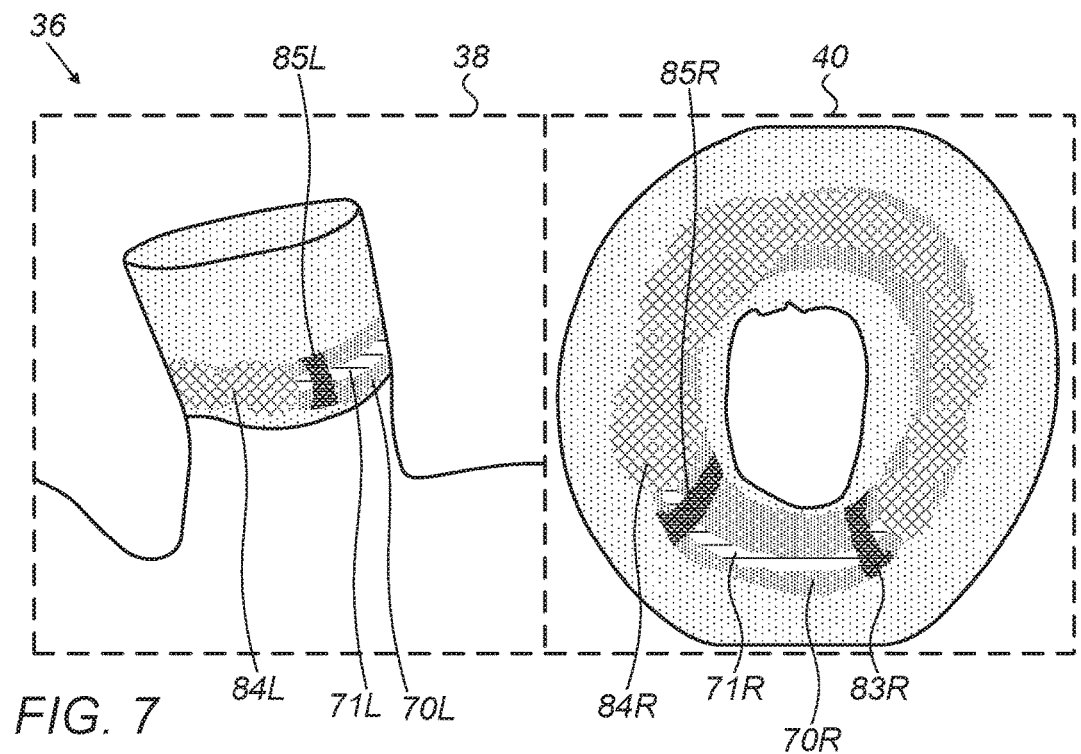

FIG. 7 illustrates on display screen 36 the progress of the ablation procedure, when over half of the circumference of pulmonary vein 16 has been covered by a contiguous ablation lesion, shown as lesion images 84L and 84R, respectively. The advantage of displaying the 2D image on right display 40, as compared with the 3D image on left display 38, for a rapid and easy assessment of the progress of the ablation procedure, is clearly seen. As is illustrated in the figure, 2D image lesion 84R displays the complete contiguous lesion, position 83R and another recommended ablation position 85R, whereas in 3D image 84L only a portion of the lesion, and one of the recommended ablation positions 85L, are visible.

Figure 8:
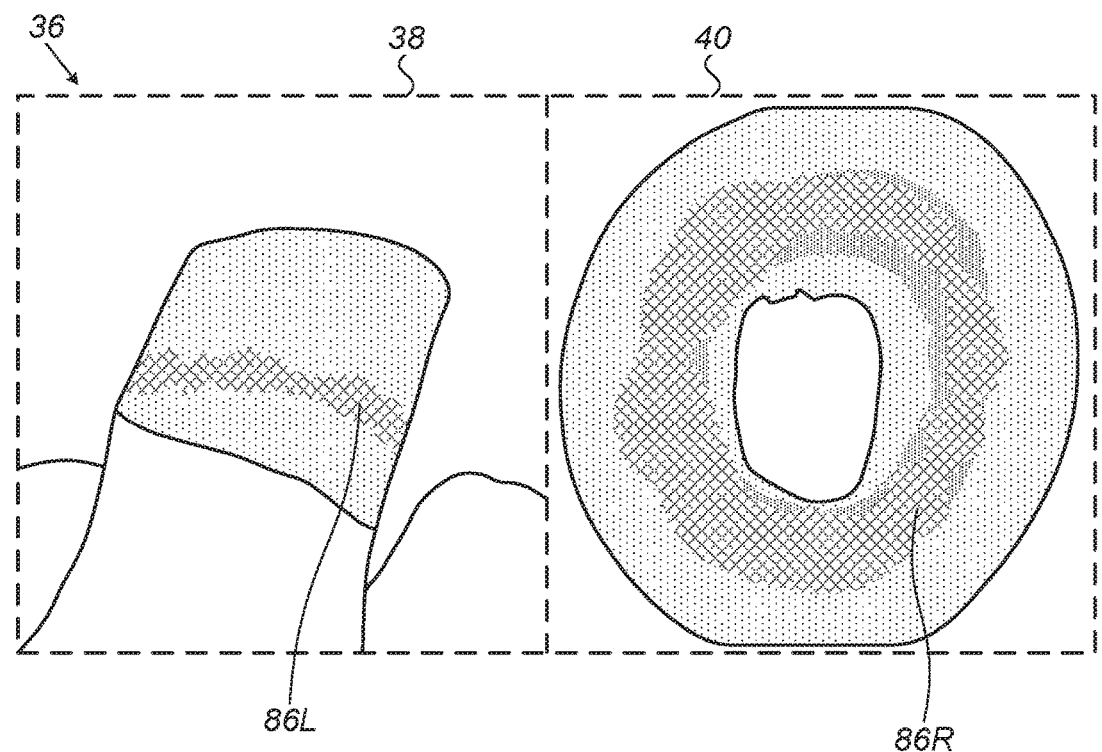

FIG. 8 illustrates the completed ablation lesion, shown as lesion images 86L and 86R. Both images display as closed paths, corresponding to the closed recommended path around the pulmonary vein illustrated in FIG. 3. However, the contiguity of the lesion is immediately visible and verifiable in the 2D image of right display 40, whereas the 3D image of left display 38 requires manipulation in order to verify the lesion contiguity.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for controlling display of data during a medical procedure, the method comprising:
   acquiring location signals indicating a location of a probe in a three-dimensional (3D) space, including a lumen, inside a body of a subject, the lumen extending lengthwise between a first circumferential edge and a second circumferential edge;
   presenting a 3D map of the 3D space including the lumen and the location of the probe at a portion of the lumen;
   transforming the 3D map of the lumen into a two-dimensional (2D) image by projecting the 3D map of the lumen onto a 2D annulus, the annulus comprising an inner circumferential edge corresponding to the first circumferential edge of the lumen in the 3D space and an outer circumferential edge corresponding to the second circumferential edge of the lumen in the 3D space;
   presenting the 2D image of the annulus on a display screen including the location of the probe at a portion of the annulus between the inner circumferential edge and the outer circumferential edge;
   presenting the location of one or more ablation lesions, presented on the 3D map, on the 2D image of the annulus;
   calculating an ablation path for the one or more ablation lesions on the lumen; and
   displaying the ablation path between the first circumferential edge and the second circumferential edge on the lumen on the 3D map and between the inner circumferential edge and the outer circumferential edge on the 2D image of the annulus.

2. The method according to claim 1, wherein presenting the 2D image comprises presenting a stationary 2D image of the annulus.

3. The method according to claim 2, comprising presenting the 3D map and the stationary 2D image simultaneously on adjacent parts of the display screen.

4. The method according to claim 3, comprising maintaining the 2D image of the annulus as a stationary image while manipulating the 3D the lumen in one or more directions on the 3D map.

5. The method according to claim 1, wherein the lumen is a pulmonary vein of a heart.

6. The method according to claim 5, further comprising determining a completion of an ablation procedure in response to presenting an image of a contiguous closed lesion on the 2D image of the annulus.

7. The method according to claim 1, further comprising:
   calculating a starting point for a further ablation lesion based on at least one of a calculated location of a previous ablation lesion and an extent of the further ablation lesion; and
   displaying the starting point as a mark on the lumen on the 3D map and on the 2D image of the annulus.

8. A processing and display apparatus for use in a medical procedure, comprising:
   a display screen; and a processor which is configured to:
   acquire location signals indicating a location of a probe in a three-dimensional (3D) space, including a lumen, inside a body of a subject, the lumen extending lengthwise between a first circumferential edge and a second circumferential edge;
   present a 3D map of the 3D space, including the lumen and the location of the probe at a portion of the lumen, on the display screen;
   transform the 3D map of the lumen into a 2D image by projecting the 3D map of the lumen onto a 2D annulus, the annulus comprising an inner circumferential edge corresponding to the first circumferential edge of the lumen in the 3D space and an outer circumferential edge corresponding to the second circumferential edge of the lumen in the 3D space;
   present the 2D image of the annulus on the display screen including the location of the probe at a portion of the annulus between the inner circumferential edge and the outer circumferential edge;
   calculate an ablation path for the one or more ablation lesions on the lumen, and
   display the ablation path between the first circumferential edge and the second circumferential edge on the lumen on the 3D map and between the inner circumferential edge and the outer circumferential edge on the 2D image of the annulus.

9. The apparatus according to claim 8, wherein the 2D image of the annulus is stationary.

10. The apparatus according to claim 8, wherein the processor is configured to present the 3D map and the stationary 2D image simultaneously on adjacent parts of the display screen.

11. The apparatus according to claim 10, wherein the processor is configured to maintain the 2D image of the annulus as a stationary image while manipulating the 3D the lumen in one or more directions on the 3D map.

12. The apparatus according to claim 8, wherein the lumen is a pulmonary vein of a heart.

13. The apparatus according to claim 12, wherein the processor is configured to determine a completion of an ablation procedure in response to presenting an image of a continuous closed lesion on the 2D image of the annulus.

14. The apparatus according to claim 8, wherein the processor is configured to:
 calculate a starting point for a further ablation lesion based on at least one of a calculated location of a previous ablation lesion and an extent of the further ablation lesion, and
 display the starting point as a mark on the lumen on the 3D map and on the 2D image of the annulus.

15. A non-transitory computer readable medium having instructions for causing a computer to perform a method of controlling display of data during a medical procedure, the method comprising:
 acquiring location signals indicating a location of a probe in a three-dimensional (3D) space, including a lumen, inside a body of a subject, the lumen extending lengthwise between a first circumferential edge and a second circumferential edge;
 presenting a 3D map of the 3D space including the lumen and the location of the probe at a portion of the lumen;
 transforming the 3D map of the lumen into a two-dimensional (2D) image by projecting the 3D map of the lumen onto a 2D annulus, the annulus comprising an inner circumferential edge corresponding to the first circumferential edge of the lumen in the 3D space and an outer circumferential edge corresponding to the second circumferential edge of the lumen in the 3D space; and
 presenting the 2D image of the annulus on a display screen including the location of the probe at a portion of the annulus between the inner circumferential edge and the outer circumferential edge;
 presenting the location of one or more ablation lesions, presented on the 3D map, on the 2D image of the annulus;
 calculating an ablation path for the one or more ablation lesions on the lumen; and
 displaying the ablation path between the first circumferential edge and the second circumferential edge on the lumen on the 3D map and between the inner circumferential edge and the outer circumferential edge on the 2D image of the annulus.

* * * * *